United States Patent [19]

Thill et al.

[11] 4,298,000
[45] Nov. 3, 1981

[54] FLUID DISPENSING DEVICE

[75] Inventors: Gary A. Thill, St. Paul, Minn.; Jerome E. Strand, St. Joseph Township, St. Croix County, Wis.

[73] Assignee: Minnesota Mining and Manufacturing Company, St. Paul, Minn.

[21] Appl. No.: 144,614

[22] Filed: Apr. 28, 1980

Related U.S. Application Data

[62] Division of Ser. No. 958,678, Nov. 8, 1978, Pat. No. 4,202,333.

[51] Int. Cl.³ .............................................. A61M 5/00
[52] U.S. Cl. ............................................... 128/218 A
[58] Field of Search .......... 128/218 A, 218 R, 218 F, 128/214 E, 214 R, 214 F, 215, 216, DIG. 12; 222/52, 70, 71, 63

[56] References Cited

U.S. PATENT DOCUMENTS

| | | | |
|---|---|---|---|
| 2,295,849 | 9/1942 | Kayden | 128/215 |
| 2,605,765 | 8/1952 | Kollsman | 128/218 R |
| 3,181,529 | 5/1965 | Wilburn | 128/216 X |
| 3,279,653 | 10/1966 | Pfleger | 128/218 A |
| 3,675,891 | 7/1972 | Reynolds et al. | 251/117 |
| 3,886,938 | 6/1975 | Szabo et al. | 128/218 A |
| 4,014,333 | 3/1977 | McIntyre | 128/214.4 X |
| 4,202,333 | 5/1980 | Thill et al. | 128/218 A |

Primary Examiner—John D. Yasko
Attorney, Agent, or Firm—Cruzan Alexander; Donald M. Sell; William L. Huebsch

[57] ABSTRACT

A dispensing device comprises a metering assembly adapted to be coupled to a conventional syringe, which metering assembly includes a long length of capillary tubing through which the fluid must pass into a flexible hose which delivers the fluid and means for applying a uniform force to the plunger to provide fluid flow through the capillary tube at a slow, steady rate over a long period of time. The metering assembly includes parts moveable between a metering position at which fluid flowing through the metering assembly must pass through the capillary tubing, and a purging position at which fluid propelled by manual operation of the syringe can bypass the capillary tube and flow rapidly through the metering assembly to purge the hose.

8 Claims, 8 Drawing Figures

FLUID DISPENSING DEVICE

This a division of application Ser. No. 958,678 filed Nov. 8, 1978 now U.S. Pat. No. 4,202,333.

BACKGROUND OF THE INVENTION

The present invention relates to devices for dispensing fluids at a slow rate for a sustained period of time, and in one important aspect to such devices used for dispensing medicinal fluids into a patient's body.

The art is replete with various devices adapted for dispensing medicinal fluids at a slow sustained rate, U.S. Pat. Nos. 2,295,849; 2,602,446; 2,605,765; 3,279,653; 3,398,860; 3,468,308; 3,469,578; 3,486,539; 3,895,631 and 3,951,147 being illustrative examples.

While the fluid dispensing devices described in these patents may with varying facility be able to dispense fluids into patients, most are more complex than may be desired, many require activation or regulation by a person attaching them which if improperly done can result in the wrong dispensing rate, and most do not provide the level of protection against inadvertent improper operation of the device of tampering with the device by the patient or another that may be desired.

SUMMARY OF THE INVENTION

The present invention provides a device for dispensing fluid at a slow, uniform rate over a sustained period of time which has a simple, inexpensive structure, is easy to use, requires no regulation or adjustment by the persons using the device, and which is well-safeguarded against tampering with or inadvertent improper operation of the device.

The dispensing device comprises a metering assembly adapted by coupled to a conventional syringe, which metering assembly includes a length of capillary tubing though which the fluid must pass into a length of flexible hose which delivers the fluid to a patient, and means for applying a uniform force to the plunger to provide fluid flow through the capillary tube at a slow, steady rate over a long period of time (e.g., in the range of 1 to 40 milliliters per hour).

The rate of flow Q in cc/sec through the capillary tube can be esitmated from Poiseuille's Law expressed in the equation:

$$Q = Pr^4/8ln$$

where P is the pressure drop through the tube dynes/cm$^2$, r is the internal radius of the tube in cm, l is the length of the tube in cm, and n is the liquid viscosity in poise.

By solving this equation it can be found that capillary tubes of a reasonable length suitable for restricting flow to rates in the range indicated under the influence of pressures of the range of pressures easily developed in a syringe (e.g., about 69,000 to 2,068,400 dynes/cm$^2$) can have bores in the range of about 0.0025 to 0.023 cm. With current technology it is difficult to produce capillary tubing in this size range with bore diameters which deviate less than about 10% from a nominal diameter, however. Since the rate of flow through a tube is proportional to the fourth power of its diameter, such a deviation could cause a variation of about $-34\%$ to $+46\%$ in flow rate, which would be unacceptable for most medical uses. By only using long lengths of capillary tubing, however, (i.e., capillary tubes over 2 centimeter in length) much less variation in flow rates is found between different lengths of capillary tubing than is suggested above; perhaps because diameter variations tend to cancel each other along the length of the capillary tubes. With capillary tubing of polytetrafluoroethylene sold under the trade designation "Teflon" (which is preferred) having a nominal inside diameter in range of 0.0025 to 0.023 cm, it has been found that lengths of the capillary tubing in excess of 2 cm. normally produce flow rate variations of less than 10%, which is acceptable for medical use of the device described herein.

Metering assemblies having capillary tubes of different nominal diameters which afford different rates of fluid flow (which rates, for example, may be indicated by color coding of the metering devices) can be used interchangeably in the device, it being contemplated that the inexpensive metering devices and the hoses attached thereto could be disposed of after use to insure sanitation for medical or other uses.

To afford purging of air from the hose attached to the metering assembly with fluid from the syringe, the metering assembly includes parts moveable between a metering position at which fluid flowing through the metering assembly must pass through the capillary tubing, and a purging position at which fluid propelled by manual operation of the syringe can bypass the capillary tube and flow rapidly through the metering assembly to purge the hose.

The device, however, insures that the metering assembly is in its metering when inserted in the dispensing device to preclude operation of the device with the metering assembly in its purge position. Support means on the device (which both supports the metering assembly and a syringe coupled thereto and is included as part of a frame for the device) is specially adapted so that it will engage and support the metering assembly only when it is in its metering position.

Also the device includes manually operated activating means which allows the syringe and the metering assembly attached thereto to be easily inserted in or removed from the device, and which secures the syringe and metering assembly in the device so they may not be tampered with when the spring means is engaged with the syringe.

The activating means includes a cover which is manually moveable between open and closed positions and is coupled to the spring means to move it to a disengaged position when the cover is opened so that a metering assembly coupled to a syringe may be inserted in the support means; and to move the spring means to an engaged position at which the spring means will apply a uniform force against the plunger of the syringe to cause fluid to flow through the metering assembly into the hose when the cover is moved to its closed position at which the cover encloses the syringe and spring means. Also included are means for releasably latching the cover in its closed position at which an edge portion of the cover will engage the metering assembly in the support means. Thus access to the syringe or removal of the metering assembly from the support means is precluded unless the cover is opened, which opening of the cover will disengage the spring means from the syringe and stop operation of the dispensing device.

BRIEF DESCRIPTION OF THE DRAWING

The device will further be described with reference to the accompanying drawings wherein like numerals refer to like parts through the several views and wherein.

DESCRIPTION OF THE PREFERRED EMBODIMENT

Figure 1:
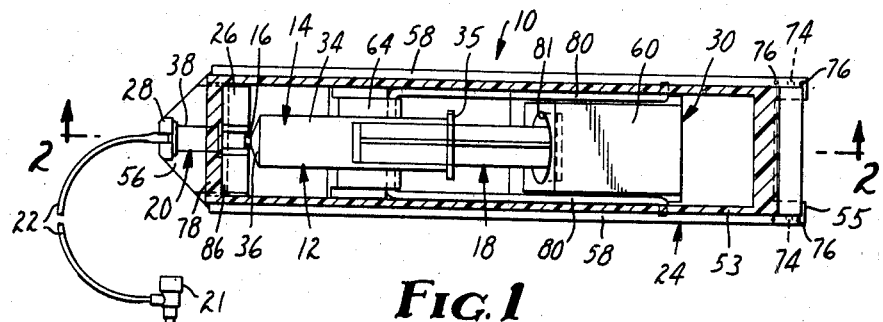
FIG. 1 is a horizontal sectional view of a fluid dispensing device according to the present invention having inserted therein a syringe from which fluid is to be dispensed.

Referring now to the drawing, there is illustrated a fluid dispensing device according to the present invention generally designated by the reference numeral 10.

The fluid dispensing device 10 is adapted to dispense fluid at a slow, steady rate over a prolonged period of time from a conventional syringe 12 of the type including an elongate housing 14 with an outlet tube 16 at one end, and a plunger 18 adapted to expel fluid within the syringe 12 through the outlet tube 16.

Briefly the device 10 includes a metering assembly 20 coupled between the syring 12 and a length of flexible hose 22 (which hose 22 is shown coupled to a needle 23 via a luer-lock fitting 21 at its end opposite the metering assembly 20 to facilitate injecting the fluid into a patient's veins or tissues, but which hose 22 alternatively could be open-ended to facilitate insertion of the hose 22 into a patient's digestive or breathing passages or have attached thereto any shape of head via the luer lock fitting portion on the hose 2 or otherwise to facilitate distributing fluids to a patient's body), which metering assembly 20 includes a capillary tube 25 (FIG. 7) through which the fluid must flow to restrict flow of fluid from the syringe 12; a support frame 24 comprising spaced fork-like members 26 and 28 for supporting the metering assembly 20 and the syringe 12; and spring means 30 for applying uniform force against the plunger 18 of the syringe 12 to press it towards the fork-like members 26 and 28 and cause fluid within the syringe 12 to flow through the metering assembly 20 and hose 22.

The syringe 12 which the dispensing device 10 is adapted to receive is of a conventional type comprising the housing 14 which includes a tubular wall 34 having an open end 35, and an end wall 36 at its end opposite the open end 35 from which projects the outlet tube 16 which defines an outlet opening for the housing 14; and the plunger 18 which has one end portion positioned within and sealing against the inner surface of the tubular wall 34 and an opposite end portion projecting from the open end 35 of the tubular wall 34, and which can have fluid within the tubular wall 34 between the end wall 36 and the plunger 18.

The metering asembly 20 includes means for bypassing the capillary tube 25 so that prior to use of the device 10, air can be purged from the metering assembly 20 and hose 22 by manual operation of the syringe 12.

Figure 6:
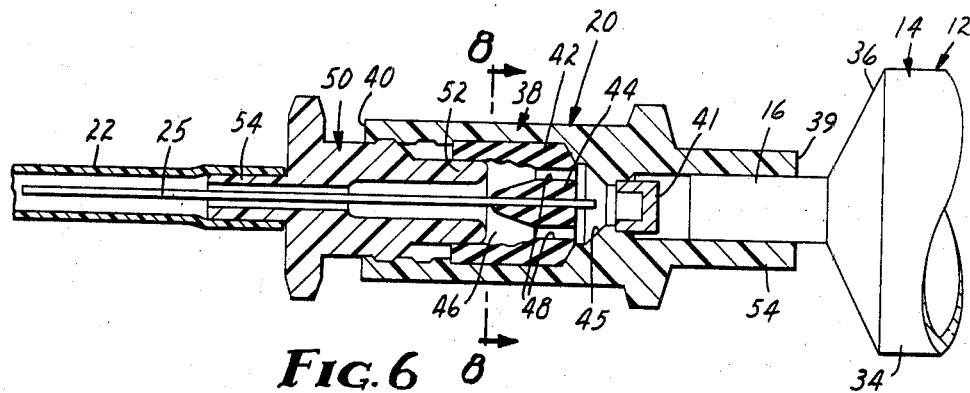
FIGS. 6 and 7 are enlarged fragmentary sectional views of the novel metering assembly included in the fluid dispensing device of FIG. 1 shown coupled to the syringe and shown respectively with parts of the metering assembly in a purging and a metering position.
Figure 7:
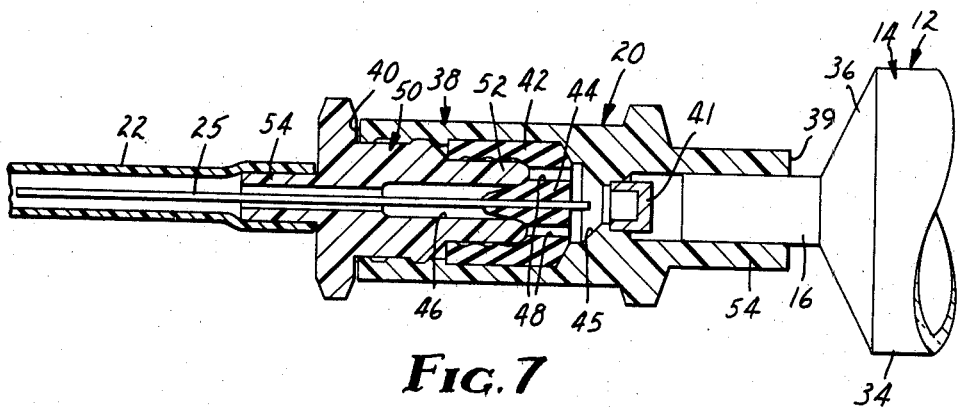
Figure 8:
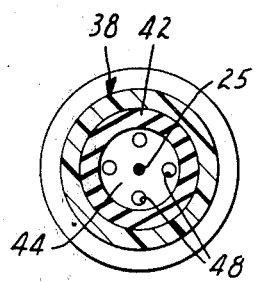
FIG. 8 is a sectional view taken approximately along line 8—8 of FIG. 6.

As is best seen in FIGS. 6 and 7, the metering assembly 20 includes a first part 38 having first and second ends 39 and 40 and a through opening between the ends 39 and 40 and having a portion adjacent its first end 39 adapted to frictionally receive the outlet tube 16 on the syringe 12 to attach the syring 12 and metering assembly 20 together. A sintered metal filter 41 is fixed to the first part 38 within its through opening and adjacent its first end 39, and a cup-like seal 42 is fixed to the first part 38 within its through opening adjacent and opening toward its second end 40. The seal 42 provides a transverse wall 44 in the through opening defining inlet and outlet chambers 45 and 46 within the first part 38 on opposite sides of the transverse wall 44. The transverse wall 44 has a plurality of through orifices 48 (FIG. 8) communicating through the transverse wall 44 between the chambers 45 and 46. One end portion of the capillary tube 25 is fixed in and extends through the transverse wall 44 and communicates with the inlet chamber 45, whereas the other end portion is unsupported and extends through the metering assembly 20 and into the hose 22 attached thereto. The metering assembly 20 also includes a second part 50 which has a through opening and has an annular tubular portion 52 sealably and movably mounted within the first part 38 for movement relative to the first part 38 between a purging position of the parts 38 and 50 at which the annular portion 52 is spaced from the orifices 48 so that fluid can flow between the chambers 45 and 46 through the orifices 48 (FIG. 6), and a metering position with the annular portion 52 of the second part 50 seated in the cup-like seal 42 and blocking the orifices 48 (FIG. 7) so that fluid in the inlet chamber 45 can pass the transverse wall 44 only through the capillary tube 25. Thus prior to insertion of the metering assembly 20 and attached syringe 12 into the frame 24, the parts of the metering assembly 20 may be positioned in their purging position to afford rapid manual purging of fluid through the metering assembly 20, hose 22, and needle 23 by manual operation of the syringe 12.

Means are provided in the device for insuring that the parts 38 and 50 of the metering assembly 20 are in their metering position when the metering assembly 20 is inserted in the dispensing device 10, thereby precluding operation of the dispensing device 10 with the metering assembly 20 in its purge position. Each of the parts 38 and 50 has a distal end portion 54 which is smaller in cross sectional area than its portion adjacent the other part 38 or 50. The slots in the fork like members 26 and 28 are sized so that they will only receive the distal end portions 54 of the parts 38 and 50. Also the pairs of fork-like members 26 and 28 are spaced sufficiently close that the distal end portions 54 will be separated by too great a distance and will not align with the fork like members 26 and 28 unless the parts 38 and 50 of the metering assembly are in their telescoped together metering position, thus precluding operation of the device 10 with the parts 38 and 50 of the metering assembly 20 in their extended purging position.

Also the device 10 includes activating means manually operated by movement of a cover 53 coupled to the spring means 30 for allowing the syringe 12 and attached metering assembly to be easily inserted in or removed from the device 10 by moving the spring means 30 to a disengaged position relative to the syringe 12 when the cover 53 is opened, and by moving the spring means 30 to an engaged position against the plunger 18 of the syringe 12 when the cover 53 is closed, and means for securing the syringe 12 and metering assembly 20 in the device 10 when the cover 53 is closed so that they may not be tampered with when the spring means is applying a uniform force to expel fluid from the syringe 12.

The frame 24 includes an elongate bar-like base portion 55 at one end of which is fixed a support member 56 including the spaced fork-like members 26 and 28 which are disposed so that they will position the syringe 12 attached to the metering assembly 20 received in the fork-like members 26 and 28 over and parallel to the base portion 55. The bar-like base portion 55 has upstanding opposed generally L-shaped rails 58 along its edges between which a hollow block 60 is mounted for movement longitudinally of the base portion 55 via four rollers 62 projecting from the edges of the block 60 adjacent the base portion 55. A plate-like slide 64 is also mounted between the rails 58 for sliding movement longitudinally of the base portion 55 between the block 60 and the member 56. A spring 66 of the type having the registered tradename "Neg'ator" has a portion 68 coiled about a hub 69 rotatably mounted within the block 60 on a shaft 70, and a straight end portion 71 extending from the block 60 to the slide 64 where it is attached by a rivet 72. The "Neg'ator" spring 66 provides a constant force attempting to wrap the entire length of the spring 66 onto its coiled portion 68, and thus provides a constant force biasing the block 60 toward the slide 64.

Figure 2:
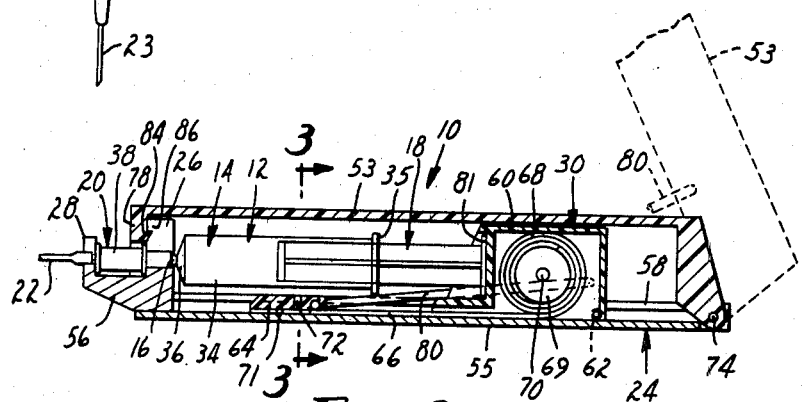
FIG. 2 is a sectional view taken approximately along line 2—2 of FIG. 1.
Figure 4:
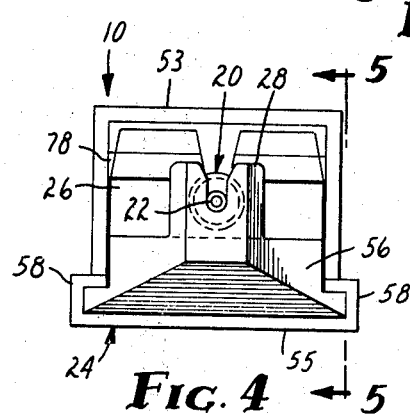
FIG. 4 is an enlarged end view of the fluid dispensing device of FIG. 1.
Figure 3:
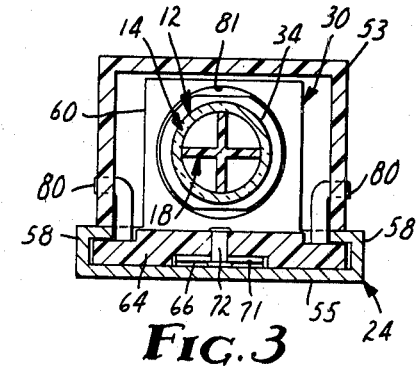
FIG. 3 is an enlarged sectional view taken approximately along line 3—3 of FIG. 2.
Figure 5:
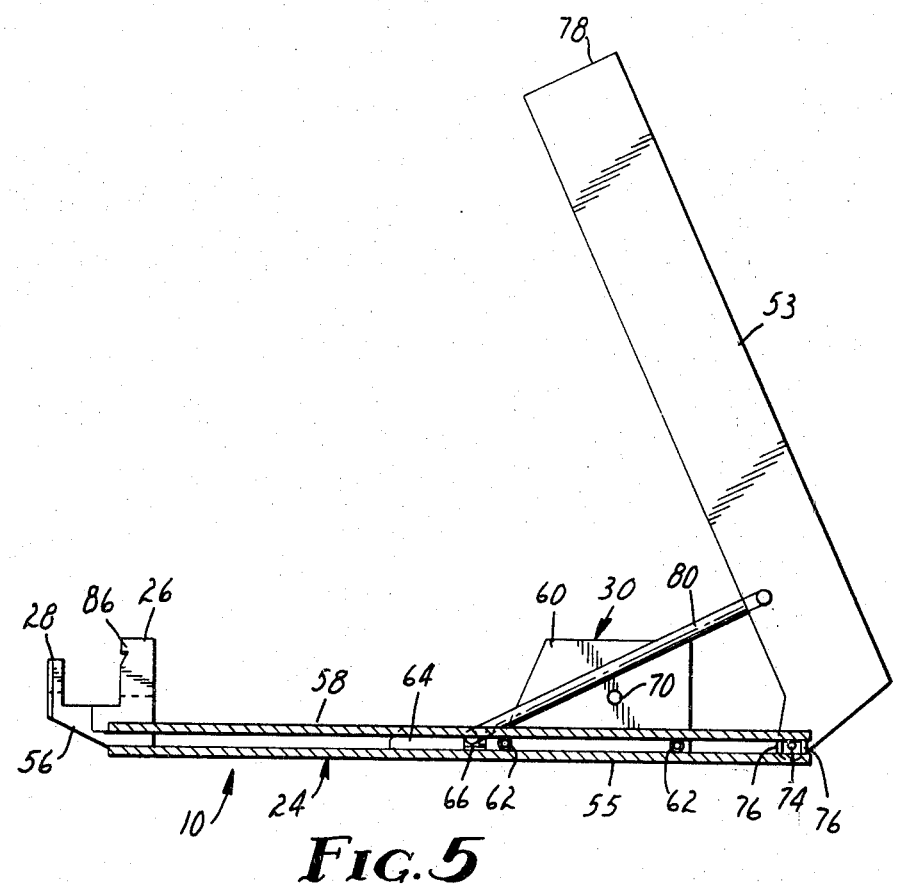
FIG. 5 is a sectional view taken approximately along line 5—5 of FIG. 4 except that a cover for the fluid dispensing device is open, and a metering device included in the device and the syringe are not inserted in the device.

The cover 53 is a rectangular box-like member of rigid transparent plastic material (preferably polysulfone) having an open side disposed adjacent the base portion 55 and having opposite outwardly projecting trunnions 74 on its end opposite the support member 56 which are pivotably mounted between the rails 58 and two pins 76 spaced along each of the rails 58 to afford pivotal movement of the cover 53 from an open position spaced from the base member 55, block 60 and syring 12 (FIG. 5); and a closed position adjacent the base member 55 enclosing the block 60 and the syringe 12 therebetween, and with an edge portion 78 of the cover 53 against the metering assembly 20 received in the fork-like members 26 and 28 to preclude their removal (FIG. 2), at which closed position the cover 53 will be retained by releasable latch means later to be explained. Parallel links 80 are pivotably mounted at their ends between the cover 53 and the slide 64, and are sized and disposed so that moving the cover 53 to its open position (FIG. 5) will move the slide 64 and block 60 to a position sufficiently spaced from the fork-like members 26 and 28 that the metering assembly 20 and attached syringe 12 may be inserted in or removed therefrom; and that moving the cover 53 to its closed position (FIG. 2) will move the slide 64 adjacent the support member 56 so that when the syringe 12 and attached metering assembly 20 are supported from the fork-like members 26 and 28, the block 60 will engage the plunger 18 on the syringe 12 during such movement with the end of the plunger received in a centering pocket 81 in the adjacent face of the block 60. Such engagement will cause the slide 64 to separate from the block 60 in opposition to the spring 66 so that while the cover 53 is closed, the spring 66 will apply a constant force against the plunger 18. Also while the cover 53 is closed, the edge portion 78 rests transversely against the metering asembly 20 and precludes its removal from between the fork-like members 26 and 28.

The means for releasably latching the cover 53 in its closed position comprises transverse mating hook-like lips 84 and 86, one of which lips 84 is a part of the cover 53 adjacent its edge portion 78, and the other of which lips is a part of the fork-like member 26 adjacent its distal end; the spring 66; and a spacing between the pins 76 that allows limited longitudinal movement of the cover 53 relative to the base portion 55 of the frame 24. When the cover 53 is being moved to its closed position and after the block 60 engages the plunger 18 of the syringe 12, the force applied by the spring 66 between the separated block 60 and slide 64 via the links 80 will press the trunnions 74 on the cover 53 against the pins 76 opposite the support member 56. As the cover approaches its closed position, cam surfaces on the lips 84 and 86 engage to move the center portion of the cover 53 toward the support member 56 and allow the hook-like lips 84 and 86 to pass each other, whereupon the spring 66 again moves the center portion of the cover 53 away from the support member 56 to engage the lips 84 and 86 as the cover 53 reaches its fully closed position. Opening the cover 53 then requires sliding it longitudinally toward the support member 56 against the bias of the spring 66 to disengage the lips 84 and 86 before the cover can be pivoted to its open position, which opening operation is not apparent from a casual inspection of the closed cover 53 and could deter unauthorized deactivation of the device 10.

As an example of the use of the fluid dispensing device 10, a person first fills the syringe 12 with a fluid to be dispensed. Next he moves the parts 38 and 50 of the metering assembly 20 to their extended purging position (FIG. 6), attaches the metering assembly 20 to the syringe 12, and manually activates the syringe 12 so that fluid flows rapidly through the orifices 48 in the metering assembly 20 and purges air from the metering assembly 20 and hose 22. Next the user telescopes the parts 38 and 50 of the metering assembly 20 together to their metering position to block the orifices 48 so that fluid can flow through the metering assembly only via the capillary tube 25, and presses the metering assembly between the fork-like members 26 and 28 with the syringe 12 projecting over the base portion 55. The user then couples the part of the fitting 21 on the hose 22 with the part on the needle 23 or a cannula (not shown) which he has previously inserted in a patient's vein or tissues, and moves the cover 53 toward its closed position so that the cover 53 via the links 80, slide 64, and spring 66 moves the block 60 into engagement with the plunger 18 on the syringe 12, after which the slide 64 is separated from the block 60 so that the spring 66 will apply a force against the plunger 18. Further movement of the cover 53 to its closed position will cause the lips 84 and 86 on the cover 53 and fork-like members 26 to cam past each other whereupon the spring 66 will maintain the lips 84 and 86 in engagement to latch the cover 53 closed. In this condition, the "Neg'ator" spring 66 will continue to apply a uniform force to cause fluid to flow at a slow uniform rate from the syringe 12 through the capillary tube 25, hose 22 and needle 23 or cannula into the patient. During this time the device 10 can be positioned in any attitude or carried on the patient to afford ambulation without affecting the fluid dispensing rate. Also tampering with the syringe 12 or metering device 20 while the fluid is being dispensed is precluded since the the syringe 12 is enclosed by the cover 53, and the metering device 20 is locked between the fork-like members 26 and 28 by the edge portion 78 of the cover, and anyone attempting to gain access to either the syringe 12 or metering device 20 will have to open the cover 53, thereby deactivating the device 10.

The present invention and its use have been explained with respect to one general type of medical use. The device may, however, be used in ways other than that indicated both for medical or other uses. For example, one or more of the devices 10 may be used to dispense fluids into a standard intravenous administration set. Also, the fluid dispensing device 10 may be used in industrial applications such as to introduce chemicals such as a catalyst into fluids moving through a continuous process, or for other uses where a small continuous supply of fluids is needed. Thus the scope of the invention should not be limited by either the structure or use of the embodiment described herein, but should be determined only by the scope of the dependent claims.

What is claimed is:

1. A dispensing device adapted for engaging fluid-filled syringe to dispense fluid from the syringe at a slow, steady rate, said device comprising a frame adapted for supporting the syringe; a hose adapted to be coupled to an outlet opening of the syringe; and an activating mechanism including a spring coupled to a block movable between a disengaged position out of engagement with the plunger of a syringe supported on the frame to afford insertion or removal of the syringe, and an engaged positon at which the block engages the plunger and the spring applies force to the plunger through the block to cause fluid within said syringe to flow into said hose, wherein the device further includes:
   a metering assembly including a first part having two chambers and an orifice communicating between said chambers; a capillary tube extending between said chambers; and a second part mounted on said first part for relative movement between a purging position spaced from said orifice so that fluid can flow between said chambers through said orifice, and a metering position blocking said orifice so that fluid can pass between said chambers only through said capillary tube;
   one of said parts being adapted to be releasably attached to the housing of the syringe with an outlet opening of the syringe communicating with one of said chambers and the hose being attached to the metering assembly with the bore of the hose communicating with the other of said chambers;
   said frame comprises support members adapted for engaging and supporting said metering assembly only when the parts of said metering assembly are in their metering position;
   said spring is adapted for applying a uniform force to move the block as the plunger moves into the syringe; and
   said activating mechanism includes structure adapted to secure the metering assembly in the support members when said activating mechanism positions said block in said engaged position.

2. A fluid dispensing device according to claim 1 wherein:
   said first and second parts are mounted for telescoping movement, said parts being extended to their purging position and being telescoped together in their metering position;
   said first and second parts have portions of reduced cross-sectional area at their opposite ends; and
   said support members are adapted to engage said portions of reduced cross-sectional area and are spaced to receive said portions of reduced cross-sectional area only when said parts are in their telescoped together metering position.

3. A fluid dispensing device accordng to claim 1 wherein said capillary tube has an inside diameter of less than about 0.023 cm. and a length of at least 2 cm.

4. A fluid dispensing device according to claim 1 wherein:
   said frame includes an elongate portion extending away from said support members;
   said support members are adapted to position a syringe attached to said metering assembly over said elongate portion;
   said block is mounted for movement along said elongate portion; and
   said activating mechanism further comprises a slide slidably mounted for movement along said elongate portion between said block and said support members with said spring being coupled between said block and said slide for applying a constant force biasing said block toward said support members upon separation of said slide and said block; a cover adapted to enclose said block and a syringe engaged with said metering assembly and projecting over said elongate portion, said cover having one end pivotably mounted at the end of said elongate portion opposite said support members for movement between an open position spaced from said elongate portion to afford insertion and removal of said metering assembly and a syringe attached thereto, and a closed position enclosing said block and the syringe with an edge portion of said cover engaging said metering assembly to retain it in said support members; and links coupled between said cover and said slide for moving said slide and block to a position spaced from the syringe when said cover is in its open position, and for moving said block into engagement with said syringe to separate said slide from said block and apply said uniform force upon movement of said cover to its closed position; said cover and said frame having lips adapted to releasably engage and latch cover in its closed position.

5. A metering assembly comprising a first part having first and second ends, and a through opening between said ends;
   a cup-like seal fixed to said first part within its through opening and opening toward its second end to provide a transverse wall in said through opening, said transverse wall having a through orifice;
   a capillary tube extending through said transverse wall; and
   a second part having first and second ends, a through opening between said ends, and an end portion adjacent its second end sealably and slidably mounted within said first part adjacent its second end for movement relative to said first part between a purging position with said end portion spaced from said orifice so that fluid can flow through the orifice in said transverse wall, and a metering position with said end portion seated in said cup-like seal and blocking said orifice so that fluid can pass said transverse wall only through said capillary tube.

6. A metering assembly according to claim 5 wherein said capillary tube has an inside diameter of less than about 0.023 cm. and a length of at least 2 cm.

7. A metering assembly according to claim 6 wherein said assembly further includes a length of hose attached to one of said first ends into which said capillary tube extends, and the first end opposite said hose is adapted to engage the outlet tube on a syringe.

8. A metering assembly according to claim 5 wherein said parts at their first ends portions of reduced cross sectional area with respect to their adjacent portions.

* * * * *

UNITED STATES PATENT AND TRADEMARK OFFICE
CERTIFICATE OF CORRECTION

PATENT NO. : 4,298,000

DATED : November 3, 1981

INVENTOR(S) : Gary A. Thill and Jerome E. Strand

It is certified that error appears in the above-identified patent and that said Letters Patent is hereby corrected as shown below:

Col. 1, line 36, "adapted by coupled" should read --adapted to be coupled--.

Col. 1, line 49, "tube dynes/cm$^2$," should read --tube in dynes/cm$^2$,--

Col. 2, line 19, "afford purging" should read --afford initial purging--.

Col. 3, line 46, "hose 2" should read --hose 22--.

Col. 6, line 17, "As the cover approaches" should read --As the cover 53 approaches--.

Col. 7, line 22, "engaging fluid" should read --engaging a fluid--.

Col. 8, line 48, "and latch cover" should read --and latch said cover--.

Col. 10, line 5, "said parts at" should read --said parts have at--

Signed and Sealed this

Twenty-third Day of July 1985

[SEAL]

Attest:

DONALD J. QUIGG

Attesting Officer

Acting Commissioner of Patents and Trademarks